United States Patent [19]
Franberg et al.

[11] Patent Number: 5,366,488
[45] Date of Patent: Nov. 22, 1994

[54] DUAL CHAMBER PACEMAKER AND METHOD FOR OPERATING SAME

[75] Inventors: Per Franberg, Stockholm; Anders Lindgren, Taeby, both of Sweden

[73] Assignee: Siemens Elema AB, Solina, Sweden

[21] Appl. No.: 22,450

[22] Filed: Feb. 25, 1993

[30] Foreign Application Priority Data

Mar. 24, 1992 [SE] Sweden .................. 9200907-5

[51] Int. Cl.$^5$ ............................................ A61N 1/00
[52] U.S. Cl. ........................................................ 607/9
[58] Field of Search ................................ 607/9, 13, 16

[56] References Cited

U.S. PATENT DOCUMENTS

| | | |
|---|---|---|
| 4,825,870 | 5/1989 | Mann et al. |
| 4,967,746 | 11/1990 | Vandegriff ........................ 607/9 |
| 4,974,589 | 12/1990 | Sholder . |
| 5,027,815 | 7/1991 | Funke et al. . |
| 5,165,405 | 11/1992 | Eckwall ............................ 607/13 |

FOREIGN PATENT DOCUMENTS

0451498 3/1991 European Pat. Off. .

*Primary Examiner*—Lee S. Cohen
*Assistant Examiner*—Marianne H. Parker
*Attorney, Agent, or Firm*—Hill, Steadman & Simpson

[57] ABSTRACT

In a dual chamber pacemaker capable of stimulating the atrium and ventricle in a heart, a stimulation pulse in the atrium could be sensed as a ventricular event which cannot be distinguished from a premature ventricular contraction, so the pacemaker institutes a blanking interval in which no sensing occurs and a crosstalk interval in which sensing occurs, detections in the crosstalk interval causing the emission of a ventricular stimulation pulse with a shortened A-V interval. A dual chamber pacemaker and a method for operating same are disclosed wherein the blanking interval is optimized so as to reduce the risk of a PVC being missed and so as also to minimize the number of detected events, caused by crosstalk from the atrium, in crosstalk intervals. This is accomplished by counting, for a number of cardiac cycles, the number of detections in crosstalk intervals and forming a relationship of the count to the number of cardiac cycles. This reduction is then used to determine the length of the blanking interval.

16 Claims, 3 Drawing Sheets

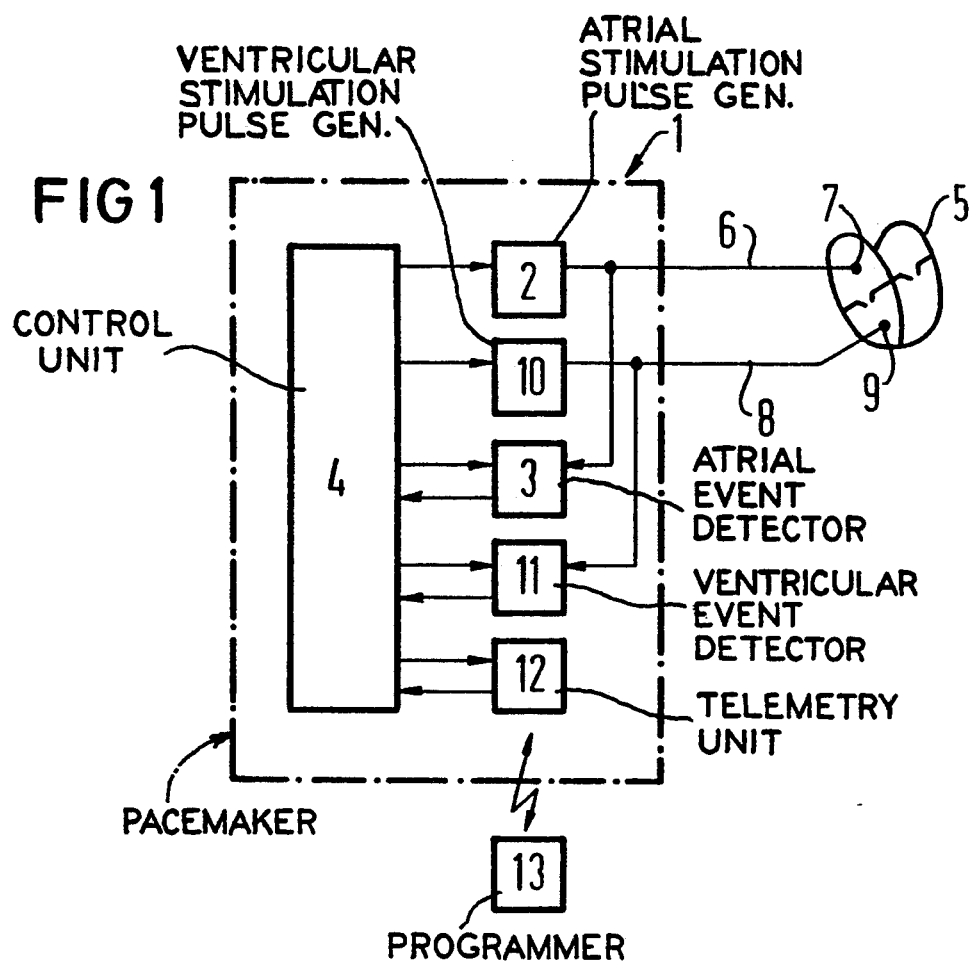
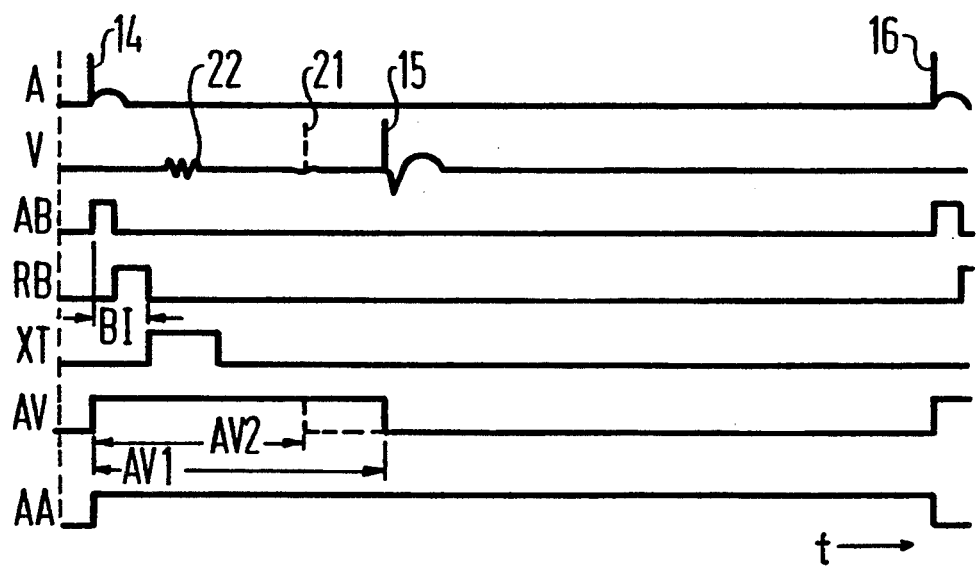

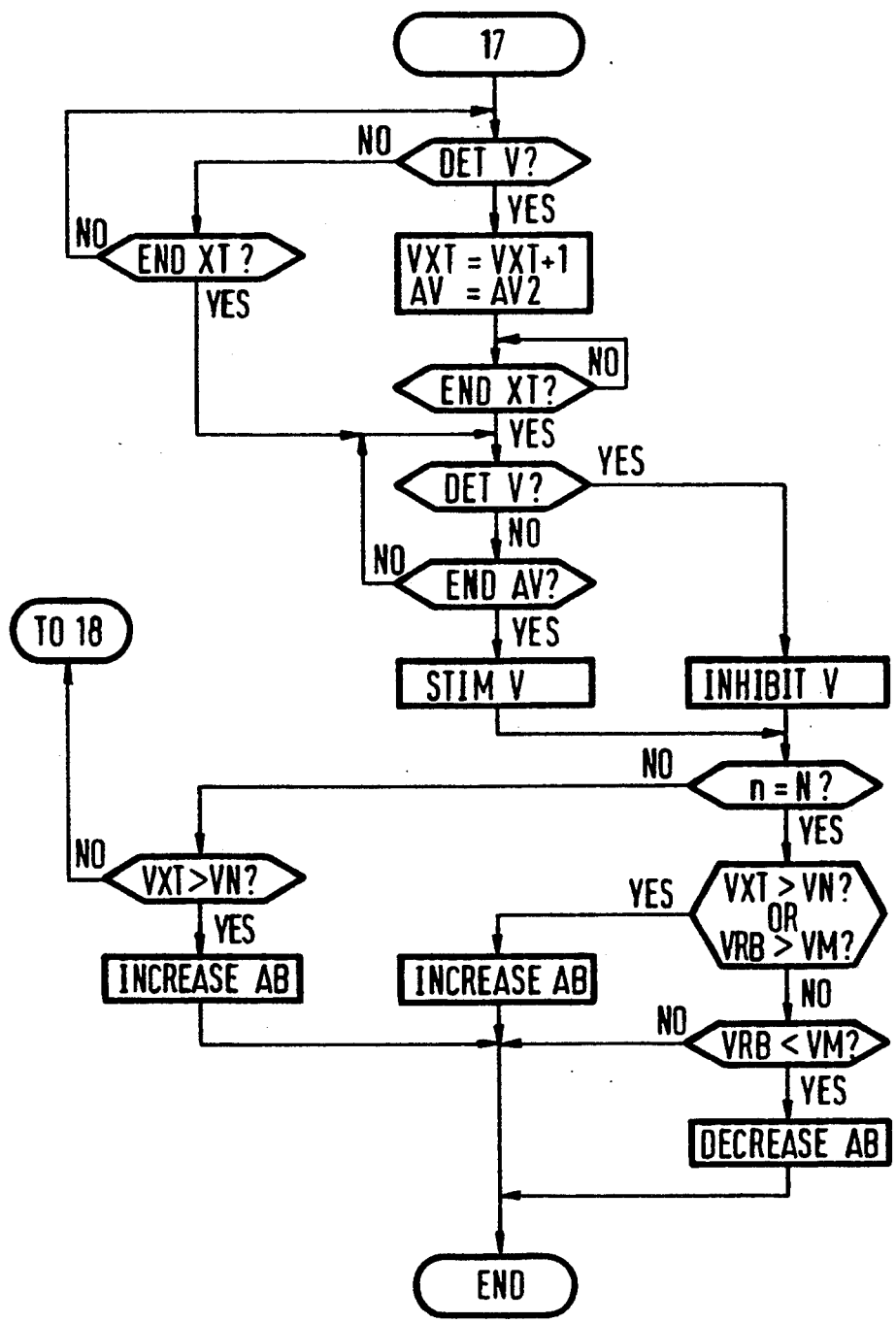

DUAL CHAMBER PACEMAKER AND METHOD FOR OPERATING SAME

BACKGROUND OF THE INVENTION

1. Field of the Invention

The present invention is directed to a dual chamber implantable pacemaker including a stimulation pulse generator which generates and emits stimulation pulses to an atrium via an atrial electrode lead and to a ventricle via a ventricular electrode lead, a detector which senses events in the ventricle and a control device which controls the stimulation pulse generator and the detector based on ventricular events detected (or not detected) within specified time intervals and a method for operating such a dual chamber pacemaker.

2. Description of the Prior Art

A dual chamber pacemaker of the type generally described above is disclosed in U.S. Pat. No. 4,825,870 wherein the control device inhibits detector sensing, after an atrial stimulation pulse has been emitted, for a preset blanking interval, orders a ventricular stimulation pulse after a lapse of a preset first A-V interval if no ventricular event is sensed between the end of the blanking interval and the end of the first A-V interval, orders emission of a ventricular stimulation pulse after a lapse of a preset second A-V interval, which is shorter than the first A-V interval, if at least one ventricular event is sensed in a preset crosstalk interval after the blanking interval, and inhibits emission of the ventricular stimulation pulse if a ventricular event is sensed after the lapse of the crosstalk interval.

This known pacemaker is capable of stimulating and sensing both in the atrium and ventricle and only stimulates when needed, i.e., when the heart itself is unable to maintain a normal rate. After every atrial event (stimulation or sensed spontaneous contraction), sensing of the ventricle is inhibited for one blanking interval, also referred to as an absolute refractory period, to prevent signals from the atrium from being interpreted as a ventricular contraction through crosstalk picked up by the detector in the ventricle. Numerous sources can give rise to crosstalk, but crosstalk from atrial stimulation pulses in particular can cause problems. The blanking interval is followed by a crosstalk interval, also referred to as a relative refractory period, during which ventricular events are sensed. However, it is impossible to determine whether events in the crosstalk interval are caused by noise or by a premature ventricular contraction (PVC). Since the sum of the blanking interval plus the crosstalk interval is selected to be less than the natural atrium-to-ventricle conduction time, i.e., the A-V interval, events in the crosstalk interval are interpreted as noise or crosstalk. As a safety measure for instances in which a PVC occurs in the crosstalk interval, the A-V interval programmed in the pacemaker is shortened. This is to prevent stimulation during the ventricle's vulnerable phase in conjunction with repolarization of cardiac tissue. In any event, the ventricular stimulation pulse is inhibited if a ventricular event occurs between the end of the crosstalk interval and the end of the programmed, or shortened, A-V interval.

One problem concerns deciding on the length of the blanking interval. The blanking interval should preferably be long enough to permit interference from the atrial stimulation pulse to abate. If it is too long, however, there is a risk that a PVC might not be detected, and a ventricular stimulation pulse could be emitted during the vulnerable phase, leading at worst to the triggering of fibrillation. On the other hand, a blanking interval which is too short often leads to detection of noise in the crosstalk interval. Ventricular stimulation with a shortened A-V interval could accordingly occur more frequently. As a result of the shorter A-V interval, a natural ventricular contraction might not have time to occur before the stimulation pulse is emitted. Unnecessary stimulation could thus occur, causing a needless energy drain on the implantable pacemaker's battery.

A pacemaker is disclosed in U.S. Pat. No. 4,974,589 in which the blanking interval can be initiated on multiple occasions during a single cardiac cycle. A first blanking interval is instituted after an atrial stimulation pulse, and a first crosstalk interval follows at the end of that blanking interval. If an event is detected within a given part of the first crosstalk interval, a second blanking interval is commenced. A second crosstalk interval starts thereafter, and a third blanking interval starts if an event is sensed within that given period. This sequence of blanking and crosstalk intervals continues until no event is sensed in the given part of the respective crosstalk interval, whereupon the crosstalk interval continues in the same way as in the pacemaker described in the aforementioned U.S. Pat. No. 4,825,870 or until a maximum period of time elapses for blanking and crosstalk intervals, all subsequent events then being interpreted as ventricular contractions.

Even if this solution does produce immediate adaptation of the blanking interval, it does not fully solve the problem of minimizing the duration of the blanking interval without emission of excessive numbers of ventricular stimulation pulses with shortened A-V intervals. In addition, a PVC could appear in one of the crosstalk or blanking intervals without being registered as anything other than noise.

SUMMARY OF THE INVENTION

It is an object of the present invention is to provide a dual chamber pacemaker which automatically sets an optimum blanking interval to minimize the risk of a PVC not being sensed, without any increase in the number of unnecessary stimulations with shortened A-V intervals.

The above object is achieved in a dual chamber constructed and operating in accordance with the principles of the present invention having a control device which, in addition to operating as described above in connection with U.S. Pat. No. 4,825,870, relates, for a number of cardiac cycles, the number of detections by the detector in the crosstalk interval to the number of cardiac cycles and orders a change in the blanking interval on the basis of the relationship obtained. The blanking interval is increased if the obtained relationship exceeds a preset relationship value and is reduced if the obtained relationship is less than the preset relationship value.

In this manner, the pacemaker automatically determines the blanking interval by relating the number of detections sensed by the detector in crosstalk intervals to the number of cardiac cycles, comparing the relationship obtained with a preset relationship value and then modifying the blanking interval. The length of the blanking interval can therefore be optimized to minimize the risk of a PVC appearing without being detected, with no increase in the number of detections, caused by atrial stimulation pulses, in the crosstalk interval. The change in the blanking interval can be made in specific steps or determined on the basis of the comparison. The preset relationship value could be, e,g., 3 detections for every 50 cardiac cycles, but it can also be set as a range, e.g., 2 to 4 detections for every 50 cardiac cycles, the blanking interval then being reduced if fewer than 2 detections are sensed and increased if more than 4 detections are sensed.

It is advantageous if the sum of the blanking interval and the crosstalk interval is constant. A total duration for these two parameters can be chosen which approximately corresponds to the spontaneous A-V conduction time, minimizing the risk of a natural ventricular event being detected in the crosstalk interval when the blanking interval has been increased.

In another embodiment of the dual chamber pacemaker according to the invention, the control device counts, for a given number of cardiac cycles, the number of detections in crosstalk intervals. The blanking interval is then increased when the number of detections exceeds a preset value, and the blanking interval is decreased when the number of detections is less than the preset value.

With a given number of cardiac cycles, the relationship is only dependent on the number of detections. The number of detections can then be allowed to govern the way in which the blanking interval is modified. An appropriate number of cardiac cycles could be 60 to 100.

Instead of having the device count the number of detections in a given number of cardiac cycles, the number of cardiac cycles could be limited to a maximum figure, the control device then comparing the number of detections in crosstalk intervals with a preset value after each cardiac cycle and increasing the blanking interval if the number of detections exceeds that preset value.

In this manner, there is no need to increase the blanking interval after a specific number of cardiac cycles. Instead, the blanking interval is increased as soon as conditions for increasing the blanking interval arise. This reduces the risk of unnecessary detections in crosstalk intervals. The maximum number of cardiac cycles could e.g., be 100. A value for the preset figure can be obtained from the preset relationship value. e.g., 3 detections in every 50 cardiac cycles as noted above, recalculated for 100 cardiac cycles, i.e., 6 detections. Therefore, if 7 detections have been registered after the fiftieth cardiac cycle, the blanking interval clearly must be increased. Instead of continuing to count another 50 cardiac cycles before the blanking interval is increased, the system institutes the increase after the first 50 cardiac cycles.

Alternatively, evaluation can be performed in such a way that the control device counts the number of cardiac cycles between two successive detections in crosstalk intervals, the blanking interval being increased when the number of cardiac cycles is less than a preset value and decreased when the number of cardiac cycles exceeds the preset value. The control device then includes means for limiting the time during which the number of cardiac cycles is counted.

Thus, the number of cardiac cycles can be used as a parameter governing modification of the blanking interval. The ability to limit the time spent on counting is necessary in case a large number of cardiac cycles is counted before the second detection occurs. The limitation could, e.g., be imposed by setting an upper limit for the number of cardiac cycles to be counted. Preferably the means for limiting cardiac cycle counting after each cardiac cycle compares the number of cardiac cycles with the preset value, and if the number exceeds the preset value the blanking interval is decreased and the counting is terminated.

In the alternative embodiment above preferably the evaluation only takes into account cardiac cycles in which atrial stimulation occurred. This leads to more accurate control of existing crosstalk. In this instance, the preset relationship value would be more relevant, since it is directly related to the instances in which crosstalk from stimulation impulses in the atrium could occur.

In a further embodiment of the dual chamber pacemaker in accordance with the invention, the control device orders a relative blanking interval constituting a part of the blanking interval, and the detector senses ventricular events in the relative blanking intervals. The control device then relates the number of detections in the relative blanking intervals to the number of cardiac cycles and the control device determines a change in the blanking interval on the basis of the obtained relationships. The blanking interval is increased if the relationship between the number of detections in the crosstalk intervals and the number of cardiac cycles exceeds the preset relationship value or if the relationship between the number of detections in the relative blanking intervals and the number of cardiac cycles exceeds a second preset relationship value. The blanking interval is decreased if the relationship between the number of detections in the crosstalk intervals and the number of cardiac cycles is less than the preset relationship value at the same time as the relationship between the number of detections in the relative blanking intervals and the number of cardiac cycles is less than the preset relationship value.

The blanking interval is subdivided in such a way that sensing takes place during part of the interval without the pacemaker regarding it as a ventricular event. i.e., no stimulation pulse is emitted after a shortened A-V interval. As a result, the tolerance level for detections in the crosstalk interval can be reduced and the length of the blanking interval optimized further. The degree of tolerance to detections in the relative blanking interval can be set relatively high, since they do not cause stimulation with a shortened A-V interval. A relationship of one i.e., one detection in the relative blanking interval for each cardiac cycle, is conceivable in extreme cases. If the length of the blanking interval is not adjusted consecutively, i.e., if there is no new counting of cardiac cycles and detections immediately after the preceding count, setting the degree of tolerance lower than one may be an advantage, e.g., as a range of 40 to 80 detections for every 100 cardiac cycles. This is because a minor physiological change in the heart could cause an increase in the duration of noise, thereby leading to a rapid rise in the number of crosstalk in the crosstalk events interval, if a long time elapses with a blanking interval minimized to such an extreme degree that every atrial stimulation pulse causes detection in the relative blanking interval.

The relative blanking interval should mainly be constant and set by a physician with a programming unit capable of communicating with the pacemaker. Similarly to the technique described above, detections in the relative blanking interval can also be used to reduce the number of cardiac cycles required to institute a change in the blanking interval.

As noted above, the counting of heart cycles and detections can be consecutive or at intervals. Consecutive counting is performed in such a way that a new count starts as soon as a relationship has been established and has been compared to the preset relationship value to determine the change in the blanking interval. Counting made at certain intervals can then be initiated by e.g., changes in amplitude and duration of the atrial stimulation pulse.

DESCRIPTION OF THE DRAWINGS

FIG. 1 is a block diagram of an embodiment of a dual chamber pacemaker constructed in accordance with the principles of the present invention.

FIG. 2 is a diagram of a cardiac cycle, describing the operation of the embodiment according to FIG. 1.

FIGS. 3a and 3b are flowcharts exemplifying one way which the embodiment of FIG. 1 may perform an evaluation in accordance with the invention.

DESCRIPTION OF THE PREFERRED EMBODIMENTS

Figure 3A:
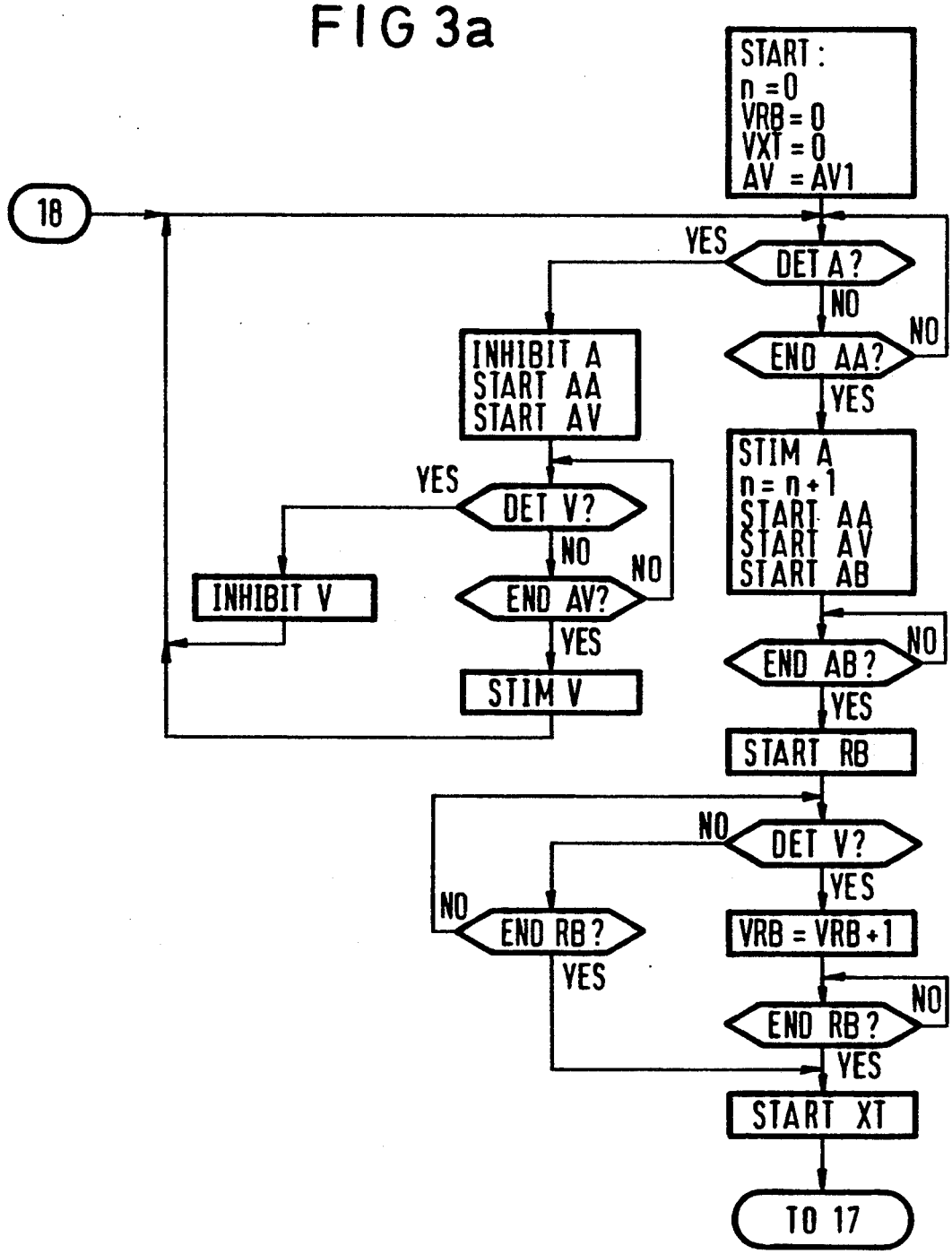

FIG. 1 shows a block diagram of a dual chamber pacemaker 1 in one embodiment according to the invention. The dual chamber pacemaker 1 includes an atrial stimulation pulse generator 2, an atrial detector 3, a ventricular stimulation pulse generator 10, a ventricular detector 11, a control unit 4 and a telemetry unit 12. The atrial stimulation pulse generator 2 generates stimulation pulses which are delivered to the atrium in the heart 5 via an atrial electrode lead 6 and atrial electrode tip 7. The ventricular stimulation pulse generator 10 generates stimulation pulses which are delivered to the ventricle in the heart 5 via a ventricular electrode lead 8 and a ventricular electrode tip 9. The pacemaker 1 can detect events, spontaneous or stimulated, in the heart 5 by sensing electrical activity. Electrical signals in the atrium are picked up by the atrial electrode tip 7 and transmitted to the atrial detector 3 via the atrial electrode lead 6. Electrical signals in the ventricle are picked up by the ventricular electrode tip 9 and transmitted to the ventricular detector 11 via the ventricular electrode lead 8. The detectors 3 and 11 analyze the electrical signals to determine whether they constitute a cardiac event and send the analysis results to the control unit 4. The control unit 4 controls the sensitivity of the detectors 3 and 11 and also governs the periods of time during which the detectors 3 and 11 are active. On the basis of detected events, or the absence of such events, the control unit 4 controls the respective emission of stimulation pulses by the stimulation pulse generators 2 and 10. The control unit 4 also controls the amplitude, duration and emission rate of the atrial and ventricular stimulation pulses. A physician, using an external programming unit 13, can check and change settings in the pacemaker 1. Communications between the control unit 4 and the programming unit 13 are transmitted via the telemetry unit 12.

The pacemaker 1 operates with an inhibiting function which ensures that no stimulation pulses are emitted as long as the heart 5 functions spontaneously with an adequate pulse rate. The rate can be checked and controlled in different ways, e.g., by checking and controlling the time elapsing between two consecutive atrial stimulations (A-A control) or by checking and controlling the time elapsing between a ventricular event and the subsequent atrial stimulation (V-A control). The ventricle is stimulated if no spontaneous event occurs within a given period of time after an atrial event (the A-V interval).

FIG. 2 illustrates the function of the pacemaker 1 in accordance with the invention. When a stimulation pulse 14 is delivered to the atrium, there is a risk of this electrical activity being detected in the ventricle and interpreted as a premature ventricular contraction (PVC). To prevent this, the control unit 4 inhibits sensing by the ventricular detector 11 for an absolute blanking interval AB, which constitutes part of a blanking interval Bl after the emitted atrial stimulation pulse 14. A relative blanking interval RB, during which the ventricular detector 11 is active and senses activity in the ventricle, also occurs in the blanking interval Bl. However, events sensed in the relative blanking interval RB are ignored by the control unit 4 and only serve as input for optimizing the duration of the blanking interval Bl as described in greater detail below. A crosstalk interval XT follows the blanking interval Bl. Events occurring in this interval may be caused by noise from atrial stimulation or by a PVC. If an event 22 is sensed in this interval, the programmed A-V interval AV1 is shortened to a shortened A-V interval AV2 (dashed line), and a ventricular stimulation pulse 21 is emitted after the shortened A-V interval AV2 has expired. Since it cannot be determined whether the event is due to a PVC, the stimulation pulse 21 is emitted as an additional safety precaution to maintain the heart's pumping function. The A-V interval AV1 is shortened to prevent stimulation in the vulnerable phase following a ventricular contraction if a PVC should be the cause of the detection. If no event occurs in the crosstalk interval XT or the remaining part of the A-V interval AV1, a ventricular stimulation pulse 15 is emitted. The pacemaker then waits for the A-A interval to end before the next atrial stimulation pulse 16 has to be emitted.

If a spontaneous ventricular event occurs after the crosstalk interval XT elapses, but before the A-V interval formed by the sum of AV1 and AV2 elapses, the control unit 4 inhibits emission of the ventricular stimulation pulse.

FIGS. 3a and 3b in combination show a flowchart describing a routine which can be performed by the pacemaker 1 in FIG. 1 for minimizing the blanking interval Bl. The flowchart only shows the steps essential to the minimization routine. In the following example, the relative blanking interval RB is constant, and the change in the blanking interval Bl is made by modifying the absolute blanking interval AB. In the start block, FIG. 3a, the number of accumulated cardiac cycles n, the number of events detected in the relative blanking interval VRB and the number of events detected in the crosstalk interval VXT are zeroed. In addition, the current A-V interval AV is set at an interval duration AV1 which corresponds to the programmed A-V interval.

In the next block (DET A?), the atrium is sensed for spontaneous events. If a spontaneous event occurs, emission of atrial stimulation pulse (INHIBIT A) is inhibited at the same time as the A-V and A-A intervals are started. Since crosstalk to the ventricle occurs after stimulation in the atrium, cardiac cycles with spontaneous atrial heart beats are not included in the evaluation. In this branch of the flowchart the ventricle is only sensed for spontaneous events (DET V?) until the A-V interval expires (END AV?). The ventricle (STIM V) is stimulated if no spontaneous event has been sensed, and the atrial sensing block then awaits the next cardiac cycle. If a spontaneous event is detected, emission of the ventricular stimulation pulse (INHIBIT V) is inhibited, and the next cardiac cycle is awaited.

If no spontaneous atrial event is sensed before the A-A interval expires (exit YES in block END AA?), the atrium is stimulated (STIM A), the number of accumulated cardiac cycles is increased by an increment of 1 (n=n+1) and the AA, AV and AB intervals are started. There is no sensing during the absolute blanking interval AB, and this interval elapses without any other functional operations. The relative blanking interval RB (START RB) is started after the lapse of the absolute blanking interval AB. The ventricle is sensed (DET V?) during this interval. As long as no event is detected the interval passes with alternative checks on events and interval time. If no event is sensed before the relative blanking interval RB expires, the crosstalk interval XT (START XT) starts. If an event is detected the number of events VRB sensed in the relative blanking interval RB is increased by an increment of 1 (VRB=VRB+1). The end of the interval is then awaited and the crosstalk interval XT starts thereafter. Evaluation only allows one registered event in the relative blanking interval RB for each cardiac cycle.

The flowchart continues in FIG. 3b with the crosstalk interval XT, FIG. 3b. If no event is detected, expiration of the interval is awaited. If an event is detected, the number of detected events VXT in the crosstalk interval is increased by an increment of 1 (VXT=VXT+1) at the same time as the A-V interval AV is set at the shortened interval duration (AV-=AV2).

After the crosstalk interval XT, the ventricle (DET V?) is sensed for the rest of the A-V interval (END AV?). If no event is detected before the A-V interval AV elapses, a ventricular stimulation pulse (STIM V) is emitted. If an event is detected emission of the stimulation pulse is inhibited (INHIBIT V).

When the A-V interval expires, a check is also made as to whether the number of accumulated cardiac cycles n has reached the number of cardiac cycles N to be covered by the evaluation. If this is not the case (exit NO in block n=N?), a check is made as to whether the number of sensed events VXT in the crosstalk interval XT has exceeded a preset permissible number of events VN for the entire evaluation (VXT>VN?). If This is the case, the evaluation does not need to run through the remaining cardiac cycles. The absolute blanking interval can be increased immediately (INCREASE AB), and evaluation ends (END). Otherwise, the next cardiac cycle is awaited.

Results are evaluated when the prescribed number of cardiac cycles N is reached. The number of events VRB in the relative blanking interval RB is compared to a preset number VM (VRB>VM?), and the number of events VXT in the crosstalk interval is compared to the preset number of permissible events VN (VXT>VN?).

If the number of events VRB in the relative blanking interval RB is greater than the preset number VM, or if the number of events VXT in the crosstalk interval XT is greater than the preset permissible number VN (exit YES block VXT>VN?; VRB>VM?), the absolute blanking interval AB is increased (INCREASE AB) and the evaluation ends (END). Otherwise, a check is made to determine whether the number of events VRB in the relative blanking interval RB is less than the preset number VM (VRB<VM?). If this is the case, the absolute blanking interval AB (DECREASE AB) is decreased and the evaluation ends (END). If the number of events VRB in the relative blanking interval RB is equal to the preset number VM, no change is made in the absolute blanking interval AB, and the evaluation ends (END).

Increases or decreases in the absolute blanking interval AB can be made in preset steps or decided in each evaluation. Evaluation can also be performed on a number of consecutive cardiac cycles with no consideration paid to whether an atrial stimulation pulse is emitted. The preset number VM and the preset permissible number VN can consist of intervals having an upper limit which the number of detections VXT and VRB must exceed for the absolute blanking interval AB to be increased and having a lower interval limit which the number of detections must fall below for the absolute blanking interval AB to be decreased. No check is necessary during the acquisition of evaluation data, but since an attempt is made to minimize the number of sensed events by changing the length of the blanking interval Bl, continuous checks would be an advantage. This is for the same reason that the relative blanking interval RB was introduced at all, since events sensed in this interval are only used for the evaluation, so the blanking interval Bl can be optimized without too many detections in the crosstalk interval XT. Also the number of detections VRB in the relative blanking interval RB could be checked in the corresponding manner after each cardiac cycle n.

There are many other suitable ways of performing the evaluation, e.g. by counting the number of cardiac cycles between two consecutive, sensed events in the crosstalk interval XT. The function may also for this kind of evaluation be designed so that only cardiac cycles with atrial stimulation are taken into account.

Although modifications and changes may be suggested by those skilled in the art, it is the intention of the inventors to embody within the patent warranted hereon all changes and modifications as reasonably and properly come within the scope of their contribution to the art.

We claim as our invention:

1. A dual chamber implantable cardiac pacemaker comprising:

first generator means for generating atrial stimulation pulses;

second generator means for generating ventricular stimulation pulses;

an atrial electrode lead connected to said first generator means and adapted for delivering said atrial stimulation pulses in vivo to the right atrium of a heart;

a ventricular electrode lead connected to said second generator means and adapted for delivering said ventricular stimulation pulses in vivo to the right ventricle of said heart and for sensing ventricular events;

detector means connected to said ventricular electrode lead for detecting said ventricular events sensed by said ventricular electrode lead; and control means, connected to said first and second generator means and to said detector means, for inhibiting said detector means, after an atrial stimulation pulse has been generated, for a preset blanking interval, and for ordering emission of a ventricular stimulation pulse after a lapse of a preset first A-V interval if no ventricular event is detected between an end of said blanking interval and an end of said first A-V interval, and for ordering generation of a ventricular stimulation pulse after a lapse of a preset second A-V interval, which is shorter than said first A-V interval, if at least one ventricular event is detected in a preset crosstalk interval after said blanking interval, and for inhibiting emission of a ventricular stimulation pulse if a ventricular event is detected after the lapse of said crosstalk interval, and for obtaining a relationship, for a number of cardiac cycles, between the number of detections by said detector means in said crosstalk interval and a number of cardiac cycles, and for ordering a change in said blanking interval by increasing said blanking interval if the obtained relationship exceeds a preset relationship value and by reducing said blanking interval if the obtained relationship is less than said preset relationship value.

2. A dual chamber pacemaker as claimed in claim 1 wherein said control means further comprising means for maintaining a sum of said blanking interval and said crosstalk interval constant.

3. A dual chamber pacemaker as claimed in claim 1 wherein said control means further comprises means for counting, for a preset number of cardiac cycles, a number of detections of ventricular events by said detector means in said crosstalk interval in said number of cardiac cycles and for increasing said blanking interval if the number of detections exceeds a preset detection number value and for decreasing said blanking interval if the number of detections is less than said preset detection number value.

4. A dual chamber pacemaker as claimed in claim 1 wherein said control means includes means for limiting a number of cardiac cycles which are monitored for obtaining said number of detections to a maximum number of cardiac cycles, and wherein said control means further is a means for comparing, after each cardiac cycle, the number of detections in the crosstalk interval accumulated thus far with a preset detection number value, and for increasing said blanking interval if the number of detections thus far exceeds said preset detection number value.

5. A dual chamber pacemaker as claimed in claim 1 wherein said control means further comprises means for counting a number of cardiac cycles between two successive detections of a ventricular event by said detector means in said crosstalk interval, and for increasing said blanking interval if the number of cardiac cycles is less than a preset cycle value and for decreasing said blanking interval if the number of cardiac cycles exceeds said preset cycle value, and wherein said control means further comprises means for limiting a time during which said number of cardiac cycles is counted.

6. A dual chamber pacemaker as claimed in claim 5 wherein said control means comprises means for comparing, after each cardiac cycle, the number of cardiac cycles with said preset cycle value, and for decreasing said blanking interval and ending said counting of cardiac cycles if the number of cardiac cycles exceeds said preset cycle value.

7. A dual chamber pacemaker as claimed in claim 1 wherein said control means comprises means for obtaining a relationship between the number of detections by said detector means in said crosstalk interval and a number of cardiac cycles in which an atrial stimulation pulses has been generated by said first generator means and delivered to the right atrium via said atrial electrode lead and for ordering a change in the blanking interval on the basis of the relationship thus obtained.

8. A dual chamber pacemaker as claimed in claim 1 wherein said control means further comprises means for setting a relative blanking interval which constitutes a part of said blanking interval, and means number of ventricular events detected by said detector means in said relative blanking interval in said number of cardiac cycles and said number of cardiac cycles, and means for changing said blanking interval by increasing said blanking interval if the relationship between the number of detected ventricular events in the crosstalk intervals of said cardiac cycles and the number of said cardiac cycles exceeds said preset relationship value or if the relationship between the number of detected ventricular events in the relative blanking intervals of said number of cardiac cycles and the number of said cardiac cycles exceeds a further preset relationship value, and by decreasing said blanking interval if said relationship between the number of detected ventricular events in said crosstalk intervals of said cardiac cycles and the number of said cardiac cycles is less than said preset relationship value while the relationship between the number of detected ventricular events in said relative blanking intervals of said cardiac cycles and the number of cardiac cycles is simultaneously less than said further preset relationship value.

9. A method for operating a dual chamber implantable cardiac pacemaker comprising the steps of:
generating and delivering in vivo an atrial stimulation pulse at controlled times in respective cardiac cycles;
generating and delivering in vivo a ventricular stimulation pulse at controlled times in respective cardiac cycles;
detecting in vivo ventricular events;
inhibiting detection of ventricular events, after an atrial stimulation pulse has been generated, for a preset blanking interval;
generating a ventricular stimulation pulse after a lapse of a preset first A-V interval if no ventricular event is detected between an end of said blanking interval and an end of said first A-V interval;
generating a ventricular stimulation pulse after a lapse of a preset second A-V interval, which is shorter than said first A-V interval, if at least one ventricular event is detected in a preset crosstalk interval after said blanking interval;
inhibiting emission of a ventricular stimulation pulse if a ventricular event is detected after the lapse of said crosstalk interval;
relating, for a number of cardiac cycles, the number of detections of ventricular events in said crosstalk interval to a number of cardiac cycles; and
changing said blanking interval on the basis of the relationship thus obtained by increasing said blanking interval if the obtained relationship exceeds a preset relationship value and by reducing said blanking interval if the obtained relationship is less than said preset relationship value.

10. A method as claimed in claim 9 comprising the additional step of maintaining a sum of said blanking interval and said crosstalk interval constant.

11. A method as claimed in claim 9 wherein the step of relating the number of detected ventricular events to a number of cardiac cycles is further defined by counting, for a preset number of cardiac cycles, the number of detections of ventricular events in said crosstalk interval in said number of cardiac cycles, and wherein the step of changing said blanking interval is further defined by increasing said blanking interval if the number of detections exceeds a preset detection number value and decreasing said blanking interval if the number of detections is less than said preset detection number value.

12. A method as claimed in claim 9 comprising the additional step of limiting the number of cardiac cycles which are monitored for obtaining said number of detections to a maximum number of cardiac cycles, wherein the step of relating the number of detected ventricular events to a number of cardiac cycles is further defined by comparing, after each cardiac cycle, the number of detections in the crosstalk interval accumulated thus far with a preset detection number value, and wherein the step of changing said blanking interval is further defined by increasing said blanking interval if the number of detections thus far exceeds said preset detection number value.

13. A method as claimed in claim 9 wherein the step of relating the number of detected ventricular events to a number of cardiac cycles is further defined by counting the number of cardiac cycles between two successive detections of a ventricular event in said crosstalk interval, wherein the step of changing said blanking interval is further defined by increasing said blanking interval if the number of cardiac cycles is less than a preset cycle value and decreasing said blanking interval if the number of cardiac cycles exceeds said preset cycle value, and wherein said method comprises the additional step of limiting the time during which said number of cardiac cycles is counted.

14. A method as claimed in claim 13 wherein the step of relating the number of detected ventricular events to a number of cardiac cycles is further defined by comparing, after each cardiac cycle, the number of cardiac cycles with said preset cycle value, and wherein the step of changing said blanking interval is further defined by decreasing said blanking interval and ending said counting of cardiac cycles if the number of cardiac cycles exceeds said preset cycle value.

15. A method as claimed in claim 9 wherein the step of relating the number of detected ventricular events to a number of cardiac cycles is further defined by relating, for a number of cardiac cycles, the number of detections of a ventricular event in said crosstalk interval to a number of cardiac cycles in which an atrial stimulation pulse is generated.

16. A method as claimed in claim 9 comprising the additional step of setting a relative blanking interval which constitutes a part of said blanking interval, wherein the step of relating the number of detected ventricular events to a number of cardiac cycles is further defined by relating the number of ventricular events detected in said relative blanking interval in said number of cardiac cycles to said number of cardiac cycles, and wherein the step of changing said blanking interval is further defined by changing said blanking interval by increasing said blanking interval if the relationship between the number of detected ventricular events in the crosstalk intervals of said cardiac cycles and the number of said cardiac cycles exceeds said preset relationship value or if the relationship between the number of detected ventricular events in the relative blanking intervals of said number of cardiac cycles and the number of said cardiac cycles exceeds a further preset relationship value, and decreasing said blanking interval if said relationship between the number of detected ventricular events in said crosstalk intervals of said cardiac cycles and the number of said cardiac cycles is less than said preset relationship value while the relationship between the number of detected ventricular events in said relative blanking intervals of said cardiac cycles and the number of cardiac cycles is simultaneously less than said further preset relationship value.

* * * * *